United States Patent [19]

Günther et al.

[11] Patent Number: 4,720,550
[45] Date of Patent: Jan. 19, 1988

[54] PROCESS FOR PRODUCING IMIDAZOLYLTHIOPHENALDEHYDES

[75] Inventors: Bernd-Rainer Günther, Bergheim; Rainer Losch, Bonn; Klaus Steiner, Pulheim, all of Fed. Rep. of Germany

[73] Assignee: A. Nattermann & CIE GmbH, Cologne, Fed. Rep. of Germany

[21] Appl. No.: 11,544

[22] Filed: Feb. 6, 1987

[30] Foreign Application Priority Data

Feb. 26, 1986 [DE] Fed. Rep. of Germany ....... 3606105

[51] Int. Cl.$^4$ .......................................... C07D 409/04
[52] U.S. Cl. ...................................... 548/336; 549/64
[58] Field of Search ......................................... 548/336

[56] References Cited

U.S. PATENT DOCUMENTS 4,643,998  2/1987  Hilboll et al. ...................... 514/252

FOREIGN PATENT DOCUMENTS 3321012  12/1984  Fed. Rep. of Germany ...... 548/336

OTHER PUBLICATIONS

*Chem. Abstracts*, vol. 65, 1966, 13686e (Sitkina, L., et al., *Khim. Geterotsikl. Soedin. Akad. Nauk Latv.* SSR 1966 (1), 143–145).
Kahn, M., et al., *J. Chem. Soc.* C., 1970, pp. 85–91.
*Chemical Abstracts*, 101:72744x (1984) [Ger. Offen. No. 3,241,102, Hilboll, et al., 5/10/84].

*Primary Examiner*—Richard A. Schwartz
*Attorney, Agent, or Firm*—Pearne, Gordon, McCoy & Granger

[57] ABSTRACT

The invention is related to a new process for producing imidazolylthiophenaldehydes of the general formula I

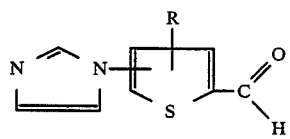

6 Claims, No Drawings

PROCESS FOR PRODUCING IMIDAZOLYLTHIOPHENALDEHYDES

The invention is related to a new process for producing imidazolylthiophenaldehydes of the general formula I

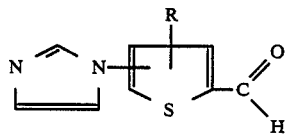

wherein R is hydrogen or methyl.

The imidazolylthiophenaldehydes of the general formula I are valuable intermediates for pharmacologically active agents such as the compound Motopizon (i.e. ±4.5-dihydro-6-[4-(1-imidazolyl)-thien-2-yl]-5-methyl-3(2H)-pyridazinone). see f.i. DE-OS No.32 41 102 (U.S. Pat. No. 4,643,998).

It is known that 5-membered heteroaromatic compounds with a free NH-group may be condensated with aryl halogenides in the presence of copper comprising catalysts to yield N-arylazoles.

L. M. Sitkina and A. M. Simonov (C.A. 65 (1966), 13686e) describe the production of 4-(1-imidazolyl)-benzaldehyde by heating imidazol and 4-bromo-benzaldehyde for 30 hours in nitrobenzol in the presence of potassium carbonate and catalytic amounts of copper-(I)-bromide at 200° C., yielding the desired 4-(1imidazolyl)-benzaldehyde in 30%.

J. B. Polya (J. Chem. Soc. C., 1970, 85 to 90) describe the production of 4-(1-imidazolyl)-acetophenone from imidazol and 4-bromoacetophenone by heating to reflux for 48 hours in pyridine in the presence of potassium carbonate and catalytic amounts of copper-(II)-oxyde yielding the desired 4-(1-imidazolyl)-acetophenone in an amount of 68%.

When transferring these process conditions to the reaction of imidazol and a bromothiophenaldehyde of general formula II

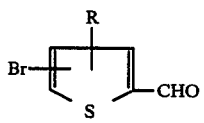

wherein R is hydrogen or methyl, and working up the reaction mixture by column chromatography, the desired imidazol-thiophenaldehydes of formula I are obtained in the unsatisfactory yield of about 2 to 20%.

It now has surprisingly been found that the desired imidazolylthiophenaldehydes of the general formula I may be prepared by a process which is significantly better than the above two processes and yield the desired final product in good yields and at a high degree of purity.

The new process is characterized in that a bromo-thiophenaldehyde of the above general formula II, in particular of 4-bromo-thiophen-2-aldehyde or 5-bromothiophen-2-aldehyde is reacted with an excess of imidazol in the presence of a copper containing catalyst in an aqueous solution at a temperature between 60° C. and reflux temperature of the reaction mixture to yield the desired imidazolylthiophenaldehydes of the above formula I or, starting from the preferred bromothiophenaldehydes above mentioned, to 4-(4-imidazolyl)-thiophen-2-aldehyde or 5-(1-imidazolyl)-thiophen-2-aldehyde. It is an essential feature of the process according to the invention that it starts from imidazol in a 2 to 8-fold excess over the amount of the started bromothiophenaldehyde. Another essential feature is carrying out the reaction in the presence of 1 to 5 l of water in relation to the amount of bromothiophenaldehyde started from. Still another essential feature and therefore most preferred is carrying out the reaction in the presence of 0.01 to 1.0 mole of metallic copper powder or a copper salt in relation to the amount of bromothiophenaldehyde started from. It is most preferred to effect the above process incorporating all of the these essential and preferred features.

It is another advantage of the process of the invention to result in a final reaction mixture which allows the recovery of bromothiophenaldehyde started from by subsequently treating the reaction mixture with hydrochloric acid and with sodium hydrogencarbonate NaHCO$_3$.

It is further preferred to subsequently purify the obtained crude imidazolylthiophenaldehyde by dissolving the crude material in chloroform and to add this chloroform solution to petrol ether with stirring.

By the process according to the invention it is possible to improve the yield of the desired imidazolylthiophenaldehyde of general formula I from 10 to 20% according to the known processes to 40 to 70%. Further, the heat input of the known processes, with a heating of the reaction mixture for 30 hours to 200° C. or for 48 hours to 130° C., in the process according to the invention is considerably lowered by a heating in the reaction mixture for 5 hours to about 100° C. Furthermore, the poisonous and unagreeable solvents nitrobenzene or pyridine are substituted by the substantially cheaper and more agreeable water as reaction solvent.

The process according to the present invention is further illustrated by the following examples. The given melting points have been determined with a Büchi 510-melting point determinator and temperatures are given in °C. non corrected.

EXAMPLE 1

4-(1H-Imidazol-1-yl)-thiophen-2-aldehyde

In a three-necked-20-l-reaction bulb aquipped with a thermometer, a reflux cooler and a KPG-stirrer, 1.911 kg (10 mole) of 4-bromothiophen-2-aldehyde, 4.084 kg (60 mole) of imidazol of 99% purity and 0.065 kg (about 1 mole) of powderous copper metal are added to 10 l of water. The reaction mixture is stirred and boiled to reflux for 5 hours. After cooling the reaction mixture to 60° C., the reaction mixture is extracted several times with a total of 26 l of chloroform. The combined chloroform solutions are washed three times mit 15 l of water. The washed chloroform phase is mixed with 10 l of water and then brought to a pH of smaller than 1 by the addition of about 750 ml of 25% hydrochloric acid with vigorous stirring. The aqueous acidic phase is added with 30 l of chloroform at 40° C. Subsequently, about 600 g of NaHCO$_3$ is added thereto slowly with vigorous stirring, until the aqueous phase reaches a pH larger than 7.5. In order to extract completely the precipitated product, the chloroform phase is separated and the aqueous phase is again extracted with 20 l of chloroform. The combined chloroform phases are evaporated to a final volume of about 4 l and is added to 9 l of petrol ether (b.p. 40° to 60° C.) with vigorous stirring. The resulting precipitate is filtered off with suction and is dried at 50° C.

Yield: 1,105 g (62% of the theoretical).

M.p.: 123° C.

Gas-chromatographical purity above 98%.

The hydrochloric chloroform phase is further processed and there are recovered 320 g of non-reacted starting material 4-bromothiophen-2-aldehyde.

The yield in 4-(1H-imidazol-1-yl)-thiophen-2-aldehyde in relation to reacted 4-bromothiophen-2-aldehyde is 74.46% of the theoretical.

EXAMPLE 2

5-(1H-Imidazol-1-yl)-thiophen-2-aldehyde 958.1 g of 5-bromothiophen-2-aldehyde, 2047 g of imidazol and 32.2 g of powderous copper metal is added to 5 l of water and the reaction mixture is boiled to reflux with stirring for 5 hours. After cooling the reaction mixture to 60° C., the reaction mixture is extracted with stirring, several times with a total of 13 l of dichloromethane. The combined dichloromethane layers are washed once with 15 l of water. The washed dechloromethane layer is mixed with 10 l of water and subsequently with about 425 ml of 25% hydrochloric acid with vigorous stirring to a pH of smaller than 1. The aqueous hydrochloric phase is mixed with 10 l of dichloromethane. Thereafter, about 345 g of sodium carbonate is added with stirring until the aqueous layer has a pH of equal or larger than 7.5. The dichloromethane layer is separated and the aqueous phase is extracted another time with 5 l of dichloromethane. The combined dichloromethane layers are evaporated to a final volume of about 4 l. Thereafter, the dichloromethane solution is poured to 9 l of petrolether (b.p. 40° to 60° C.) with stirring. The resulting precipitate is filtered off with suction and is dried at 50° C.

Yield: 429 g (48% of the theoretical).

M.p.: 105° to 107° C.

By processing the dichloromethane phase, 203 g of the non-reacted starting material 5-bromothiophen-2-aldehyde is recovered. In relation to 5-bromothiophen-2-aldehyde actually reacted, the yield in the desired final product is 60.9% of the theoretical.

Analogously to examples 1 and 2 there are produced:

4-(1H-Imidazol-1-yl)-3-methyl-thiophen-2-aldehyde.

M.p.: 149° C.

4-(1H-Imidazol-1-yl)-5-methyl-thiophen-2-aldehyde.

M.p.: 92° to 94° C.

We claim:

1. Process for producing imidazoylthiophenaldehydes of the general formula I

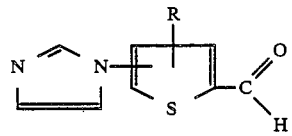

wherein R is hydrogen or methyl, comprising reacting a bromothiophenaldehyde of the general formula II

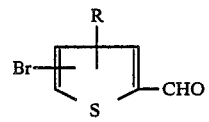

wherein R is hydrogen or methyl, with imidazole present in a molecular excess, in the presence of a copper containing catalyst in aqueous medium at a temperature between 60° C. and the reflux temperature of the reaction mixture.

2. Process according to claim 1 wherein imidazole is present in a 2 to 8-fold excess in relation to the bromothiophen-2-aldehyde of general formula II.

3. Process according to claim 1 wherein the reaction is carried out in 1 to 5 l of water as reaction solvent per mole of the bromothiophenaldehyde of general formula II started from.

4. Process according to claim 1 wherein the reaction is carried out in the presence of 0.01 to 1.0 mole of powdered copper metal or of a copper salt as catalyst per mol of the bromothiophenaldehyde of general formula II started from.

5. Process according to claim 1 wherein unreacted bromothiophenaldehyde starting material is recovered from the reaction mixture in that the reaction mixture is treated with hydrochloric acid and, subsequently, with NaHCO$_3$.

6. Process according to claim 1 wherein the resulting 1-imidazolyl-thiophenaldehyde is purified by adding the chloroform solution thereof to petroleum ether with stirring.

* * * * *